United States Patent [19]

van Geel et al.

[11] Patent Number: 5,355,394

[45] Date of Patent: Oct. 11, 1994

[54] METHOD FOR PRODUCING ACTINIUM-225 AND BISMUTH-213

[75] Inventors: Jacobus N. C. van Geel, Oberweier, Netherlands; Jean J. Fuger, Wössingen, Belgium; Lothar Koch, Weingarten, Fed. Rep. of Germany

[73] Assignee: European Atomic Energy Community (EURATOM), Plateau Du Kirchberg, Luxembourg

[21] Appl. No.: 916,835

[22] PCT Filed: Feb. 18, 1991

[86] PCT No.: PCT/EP91/00306

§ 371 Date: Aug. 10, 1992

§ 102(e) Date: Aug. 10, 1992

[87] PCT Pub. No.: WO91/13443

PCT Pub. Date: Sep. 5, 1991

[30] Foreign Application Priority Data

Feb. 23, 1990 [LU] Luxembourg ............... 87684

[51] Int. Cl.$^5$ .......................................... G21G 1/02
[52] U.S. Cl. .................................. 376/189; 376/170; 423/3; 423/249
[58] Field of Search ............... 376/170, 189, 187; 423/3, 6, 7, 249, 250

[56] References Cited

U.S. PATENT DOCUMENTS

| | | | |
|---|---|---|---|
| 2,632,763 | 3/1953 | Hagemann | 376/170 |
| 2,723,901 | 11/1955 | Hagemann et al. | 376/170 |
| 2,873,170 | 2/1959 | Hyde et al. | |
| 2,887,358 | 5/1959 | Higgins et al. | 376/170 |
| 3,269,915 | 8/1966 | Ransohoff et al. | 376/170 |
| 3,459,634 | 8/1969 | Ruiz et al. | 376/170 |
| 3,884,718 | 5/1975 | Deaton et al. | 136/83 R |
| 4,454,106 | 6/1984 | Gansow et al. | |
| 4,663,129 | 5/1987 | Atcher et al. | |

OTHER PUBLICATIONS

W. A. Müller, Radiochimica Acta 9, 4 (1968), pp. 181 to 186.

M. Monsecour, P. De Regge, L. H. Baetsle, Journal of Radioanalytical Chemistry, 35 (1977), pp. 185 to 192, 194–196.

Soviet Atomic Energy, vol. 32, No. 2, (Feb. 1972) Karalova et al, pp. 133–136.

*Primary Examiner*—Behrend E. Harvey
*Attorney, Agent, or Firm*—Sughrue, Mion, Zinn, Macpeak & Seas

[57] ABSTRACT

The invention relates to a method for producing actinium-225 and bismuth-213. According to the invention, radium-226 is irradiated in the thermal neutron flux of a nuclear reactor, the thorium fraction of the irradiation product is then chemically isolated and therefrom the actinium and radium mixture growing continuously by decay therein is chemically separated, this mixture serving as "cow" for the desired radionuclides which are growing continuously.

2 Claims, 2 Drawing Sheets

METHOD FOR PRODUCING ACTINIUM-225 AND BISMUTH-213

The invention refers to a method for producing actinium-225 and bismuth-213.

Radiotherapeutic methods for locally fighting against cancer (metastases) become more and more important in view of progresses obtained in the molecular biology field. Generally speaking, alpha-radiating nuclides of a short half-lifetime are thereby integrated into monoclonal antibodies which, after having been inserted into the body of a patient, tend to be incorporated into malign cells and destruct these cells due to an intensive irration of very short range. The radionuclide must in this case reply to particular requirements: It must be apt to be linked for conjugation to a convenient antibody, it must have a short half-lifetime (in the range of some hours) and its decay products must show a rather low chemical and radiological impact.

Among the possible candidates for such radionuclides actinium-225 and bismuth are particularly important, the relevant bismuth isotopes being either the isotope Bi-212 (half-lifetime 60,6 minutes) or the isotope Bi-213 (half-lifetime 47 minutes). The production of Bi-212 for medical use has been described in the periodical Ing. J.Nucl.Med.Biol. 9(1982), page 83. However, this isotope suffers from producing as a decay product a thallium isotope which is gamma-active and which causes an undesired radiation-strain for the patient.

This does not apply to Bi-213, but this isotope is not available in sufficient quantities and cannot, until now, be produced in such quantities from U-233 at a reasonable expenditure. This uranium isotope U-233 is transformed via several decay steps into actinium-225 and the latter finally into Bi-213.

The decisive drawback of this decay chain resides in the small available quantity of Th-229 which is derived by decay from U-233. Since, for a significant hospital supply, between 10 and 100 g of Th-229 is required, U-233 should be available in a quantity of about 1 ton and with a storage time of 20 to 30 years in view of the separation. But such quantities of U-233 do not even exist on a world-wide scale.

The invention thus aims to indicate a method allowing to produce at a reasonable price sufficient quantities of actinium-225 and bismuth-213 for therapeutical use.

The method according to the invention consists in irradiating radium in the thermal neutron flux of a nuclear reactor, in chemically separating the thorium content from the irradiated product and in chemically separating therefrom the radio nuclides radium-225 and actinium-225 obtained in a continuous way by decay from thorium-229, said radio nuclides radium-225 and actinium-225 serving as basic substance ("cow") for the nuclides actinium-225 and bismuth-213.

Preferably, the radium is submitted to a high thermal neutron flux of about $5 \times 10^{14}/cm^2 sec$.

The invention will now be described in detail by means of an example.

Figures 1, 2:
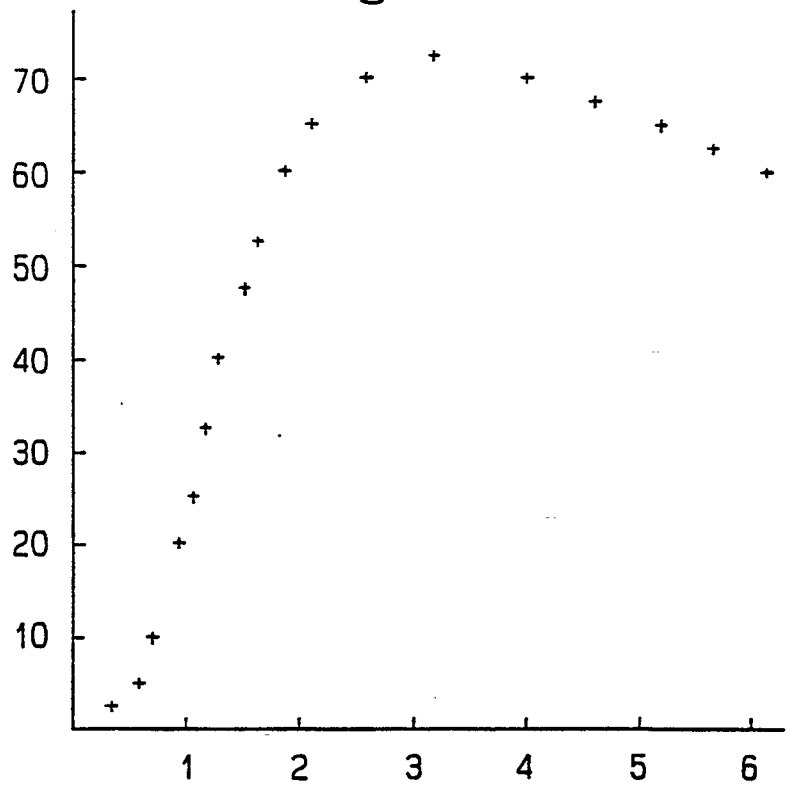
FIG. 1 shows the natural decay chain leading to bismuth-213.
FIG. 2 shows the formation of thorium-229 (in grams) as a function of time (in years) by irradiating 1 kg radium-226 in a thermal flux of $4.7 \times 10^{14}$ neutrons/$cm^2$sec.

FIG. 1 indicates the decay chain from thorium-229 to bismuth-213. At the upper end of this decay chain, there is also indicated with the atomic number 92 the isotope U-233 from which the desired thorium-229 is derived by natural decay, but, as said above, in an insufficient quantity. The key for producing Ac-225 and Bi-213 in significant quantities would be found if the isotope Th-229 could be produced in another way than by decay of U-233.

Figure 3:
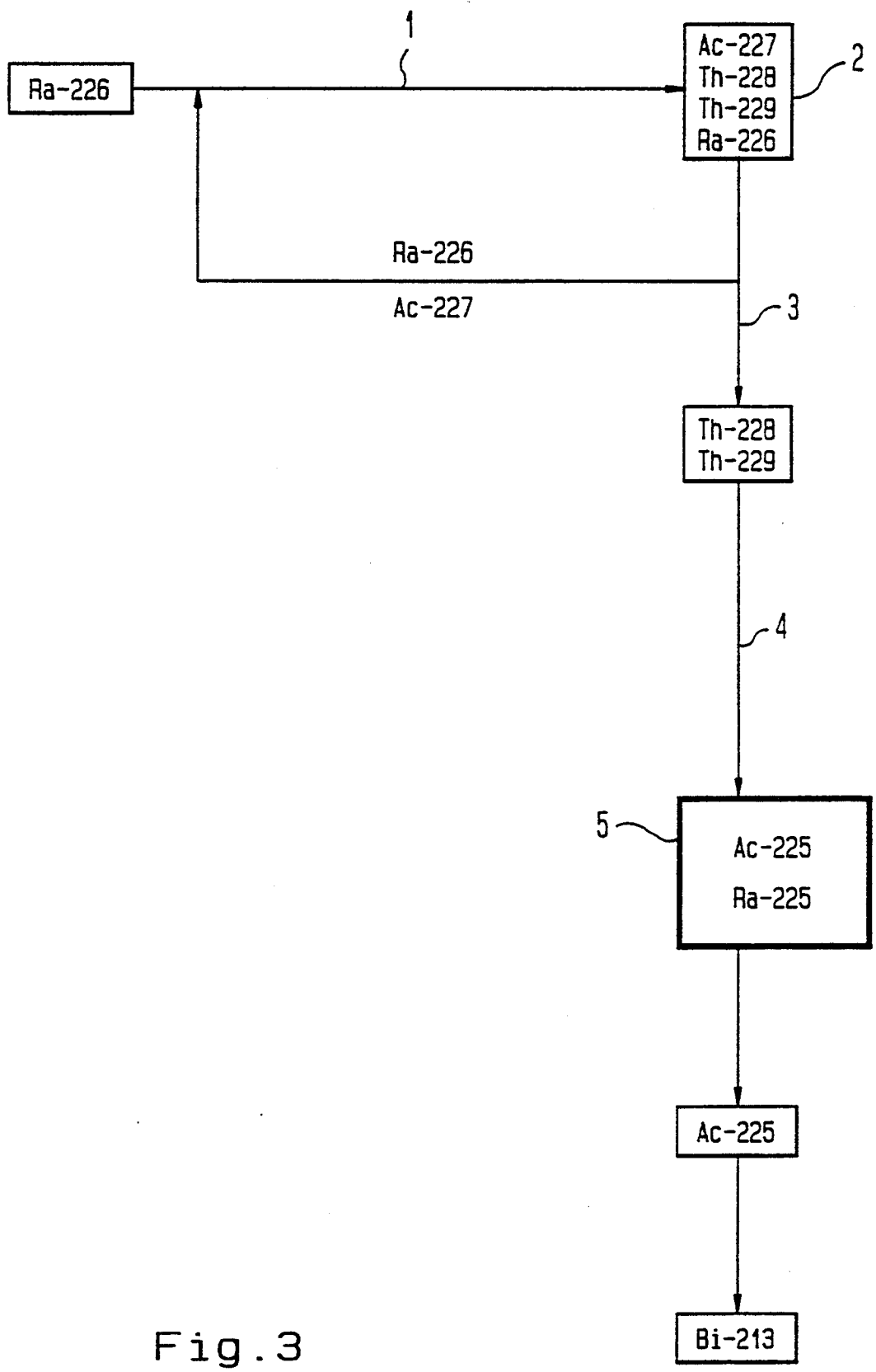
FIG. 3 shows schematically the entire method according to the invention.

As it is shown in FIG. 3, according to the invention, the basic product is not U-233, but radium-226 having an atomic number of 88. For producing 100 g of thorium Th-229, about 1 kg of radium 226 is needed. This basic product is exposed for some years, e. g. three years, a high flux reactor, to a thermal neutral flux, which is as intense as possible, of about $4.7 \times 10^{14}$ neutrons/$cm^2$sec. This is indicated in FIG. 3 by an arrow 1. By this means, among other products, radium-227 is produced which is transformed in a first stage by beta decay into Ac-227. By intercepting another neutron actinium-228 is produced, which decays with a half-lifetime of 6,13 hours into Th-228. By a further neutron bombardment, this isotope converts finally into the desired isotope Th-229. It can be shown by calculation that the irradiation of the indicated quantity of radium in a neutron flux of the above mentioned intensity over a time interval of 3 years ensures an output of Th-229 of the above mentioned quantity range (see FIG. 2).

The final product 2 of the irradiation thus consists in a mixture of radium-226 and the decay products Ac-227, Th-228 and Th-229.

From this mixture, first of all the thorium fraction is chemically separated. In this fraction, the desired radionuclides Ac-225 and Bi-213 are formed according to the decay scheme based on Th-229 as shown in FIG. 1.

It is apparent to isolate the isotope Ac-225 from the thorium fraction and to separate the isotope Bi-213 from Ac-225 which grows therein. However, in order to achieve a maximum output in Ac-225 and Bi-213, not only Ac-225 but also its mother Ra-225 (together with Ra-224 which is derived by decay from Th-228) is separated (arrow 4). Such a "cow" 5 is a continuous supplier of Ac-225 and Bi-213. Both, Ac-225 and the mixture of radium isotopes can be expedited without problems and can further be treated in clinical operation as "cow".

From this mixture of nuclides the radiotherapeutically important nuclide actinium-225 is separated, which, according to the decay chain in FIG. 1, can also be used for producing the radiotherapeutically important isotope Bi-213.

We claim:

1. A method for producing a mixture of actinium-225 and radium-225, which mixture is a basic product for obtaining bismuth-213, comprising the steps of irradiating radium-226 in a thermal neutron flux of a nuclear reactor to obtain an irradiation product comprising thorium-229, chemically isolating a thorium fraction from the irradiation product, and chemically separating from the thorium fraction radionuclides actinium-225 and radium-225 obtained by decay of thorium-229 to thereby recover a mixture of actinium-225 and radium-225.

2. A method according to claim 1, characterized in that the radium is submitted to a high thermal neutron flux of at least $4.7 \times 10^{14}$ neutrons/$cm^2$sec.

* * * * *